(12) United States Patent
Pathak

(10) Patent No.: US 8,557,535 B2
(45) Date of Patent: *Oct. 15, 2013

(54) METHODS FOR PREPARATION OF PLATELET RICH PLASMA

(75) Inventor: Chandrashekhar P. Pathak, Austin, TX (US)

(73) Assignee: Incept LLC, Lexington, MA (US)

( * ) Notice: Subject to any disclaimer, the term of this patent is extended or adjusted under 35 U.S.C. 154(b) by 589 days.

This patent is subject to a terminal disclaimer.

(21) Appl. No.: 12/555,970

(22) Filed: Sep. 9, 2009

(65) Prior Publication Data

US 2010/0069613 A1    Mar. 18, 2010

Related U.S. Application Data

(60) Continuation of application No. 11/725,751, filed on Mar. 20, 2007, now Pat. No. 7,605,232, which is a continuation of application No. 10/293,453, filed on Nov. 13, 2002, now Pat. No. 7,211,651, which is a continuation of application No. 10/068,807, filed on Feb. 5, 2002, now Pat. No. 6,887,974, which is a division of application No. 09/147,897, filed as application No. PCT/US97/16897 on Sep. 22, 1997, now abandoned.

(60) Provisional application No. 60/026,526, filed on Sep. 23, 1996, provisional application No. 60/039,904, filed on Mar. 4, 1997, provisional application No. 60/040,417, filed on Mar. 13, 1997.

(51) Int. Cl.
| | |
|---|---|
| *C12Q 1/56* | (2006.01) |
| *A61K 35/16* | (2006.01) |
| *A61K 51/08* | (2006.01) |
| *C07K 16/36* | (2006.01) |
| *A61P 7/08* | (2006.01) |

(52) U.S. Cl.
USPC ....... 435/13; 530/382; 530/388.25; 424/1.69; 514/15.3

(58) Field of Classification Search
None
See application file for complete search history.

(56) References Cited

U.S. PATENT DOCUMENTS

| | | |
|---|---|---|
| 2,533,004 A | 12/1950 | Ferry et al. |
| 3,520,949 A | 7/1970 | Shepherd et al. |
| 4,101,380 A | 7/1978 | Rubinstein et al. |
| 4,359,049 A | 11/1982 | Redl et al. |
| 4,362,567 A | 12/1982 | Schwarz et al. |
| 4,414,976 A | 11/1983 | Schwarz et al. |
| 4,565,784 A | 1/1986 | Franzblau et al. |
| 4,601,286 A | 7/1986 | Kaufman |
| 4,631,055 A | 12/1986 | Redl et al. |
| 4,646,730 A | 3/1987 | Schonfeld et al. |
| 4,670,417 A | 6/1987 | Iwasaki et al. |
| 4,735,616 A | 4/1988 | Eibl et al. |
| 4,874,368 A | 10/1989 | Miller et al. |
| 4,902,281 A | 2/1990 | Avoy |
| 4,909,251 A | 3/1990 | Seelich |
| 4,932,942 A | 6/1990 | Maslanka |
| 4,937,270 A | 6/1990 | Hamilton et al. |
| 4,938,763 A | 7/1990 | Dunn et al. |
| 4,978,336 A | 12/1990 | Capozzi et al. |
| 5,024,742 A | 6/1991 | Nesburn et al. |
| 5,030,215 A | 7/1991 | Morse et al. |
| 5,041,292 A | 8/1991 | Feijen |
| 5,059,424 A * | 10/1991 | Cartmell et al. ............... 424/443 |
| 5,104,909 A | 4/1992 | Grasel et al. |
| 5,116,315 A | 5/1992 | Capozzi et al. |
| 5,143,662 A | 9/1992 | Chesterfield et al. |
| 5,162,430 A | 11/1992 | Rhee et al. |
| 5,192,743 A | 3/1993 | Hsu et al. |
| 5,292,362 A | 3/1994 | Bass et al. |
| 5,296,518 A | 3/1994 | Grasel et al. |
| 5,304,595 A | 4/1994 | Rhee et al. |
| 5,318,524 A | 6/1994 | Morse et al. |
| 5,324,775 A | 6/1994 | Rhee et al. |
| 5,328,955 A | 7/1994 | Rhee et al. |
| 5,368,563 A | 11/1994 | Lonneman et al. |
| 5,395,923 A | 3/1995 | Bui-Khac et al. |
| 5,399,351 A | 3/1995 | Leshchiner et al. |
| 5,405,607 A | 4/1995 | Epstein et al. |
| 5,410,016 A | 4/1995 | Hubbell et al. |
| 5,413,791 A | 5/1995 | Rhee et al. |
| 5,419,491 A | 5/1995 | Breitsprecher |

(Continued)

FOREIGN PATENT DOCUMENTS

| | | |
|---|---|---|
| EP | 0557199 | 8/1993 |
| WO | 91/09641 A1 | 7/1991 |

(Continued)

OTHER PUBLICATIONS

Achterbreg et al., "Hydroactive Dressings and Serum Proteins: An In Vitro Study," J Wound Care 5:79-82 (1996) (abstract).

(Continued)

*Primary Examiner* — Satayanarayana R Gudibande
(74) *Attorney, Agent, or Firm* — Dardi & Herbert, PLLC; Curtis B. Herbert

(57) ABSTRACT

A method of preparing a fibrinogen rich composition is disclosed. One embodiment of the method involves contacting plasma with a hydrogel capable of increasing in mass upon contact with said plasma; maintaining said contact for a period of time sufficient for said hydrogel to absorb a substantial amount of at least the water from said plasma to produce a swollen hydrogel and a fibrinogen rich phase; and separating said fibrinogen rich phase from said swollen hydrogel; whereby said fibrinogen rich composition is produced.

14 Claims, 7 Drawing Sheets

(56) References Cited

U.S. PATENT DOCUMENTS

| | | |
|---|---|---|
| 5,426,148 A | 6/1995 | Tucker |
| 5,446,090 A | 8/1995 | Harris |
| 5,446,091 A | 8/1995 | Rhee et al. |
| 5,455,027 A | 10/1995 | Zalipsky et al. |
| 5,470,911 A | 11/1995 | Rhee et al. |
| 5,474,540 A | 12/1995 | Miller et al. |
| 5,475,052 A | 12/1995 | Rhee et al. |
| 5,476,909 A | 12/1995 | Kim et al. |
| 5,505,704 A | 4/1996 | Pawelka et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,550,187 A | 8/1996 | Rhee et al. |
| 5,565,519 A | 10/1996 | Rhee et al. |
| 5,567,435 A | 10/1996 | Hubbell et al. |
| 5,573,934 A | 11/1996 | Hubbell et al. |
| 5,582,596 A | 12/1996 | Fukunaga et al. |
| 5,583,114 A | 12/1996 | Barrows et al. |
| 5,585,007 A * | 12/1996 | Antanavich et al. .......... 210/782 |
| 5,605,541 A | 2/1997 | Holm |
| 5,614,587 A | 3/1997 | Rhee et al. |
| 5,626,863 A | 5/1997 | Hubbell et al. |
| 5,643,464 A | 7/1997 | Rhee et al. |
| 5,644,049 A | 7/1997 | Giusti et al. |
| 5,656,035 A | 8/1997 | Avoy |
| 5,672,622 A | 9/1997 | Hedgepeth et al. |
| 5,702,361 A | 12/1997 | Evans et al. |
| 5,741,223 A | 4/1998 | Janzen et al. |
| 5,744,545 A | 4/1998 | Rhee et al. |
| 5,749,968 A | 5/1998 | Melanson et al. |
| 5,752,974 A | 5/1998 | Rhee et al. |
| 5,762,620 A | 6/1998 | Cartmell et al. |
| 5,773,025 A | 6/1998 | Baichwal |
| 5,786,421 A | 7/1998 | Rhee et al. |
| 5,800,541 A | 9/1998 | Rhee et al. |
| 5,807,581 A | 9/1998 | Rosenblatt et al. |
| 5,810,885 A | 9/1998 | Zinger |
| 5,844,023 A | 12/1998 | Tomka |
| 5,874,500 A | 2/1999 | Rhee et al. |
| 5,932,462 A | 8/1999 | Harris et al. |
| 5,936,035 A | 8/1999 | Rhee et al. |
| 5,951,583 A | 9/1999 | Jensen et al. |
| 6,033,654 A | 3/2000 | Stedronsky et al. |
| 6,046,305 A | 4/2000 | Choi |
| 6,051,248 A | 4/2000 | Sawhney et al. |
| 6,051,648 A | 4/2000 | Rhee et al. |
| 6,110,484 A | 8/2000 | Sierra |
| 6,124,273 A | 9/2000 | Drohan et al. |
| 6,150,505 A | 11/2000 | Marx et al. |
| 6,156,531 A | 12/2000 | Pathak et al. |
| 6,162,241 A | 12/2000 | Coury et al. |
| 6,201,065 B1 | 3/2001 | Pathak et al. |
| 6,214,966 B1 | 4/2001 | Harris |
| 6,251,382 B1 | 6/2001 | Grennwald et al. |
| 6,258,351 B1 | 7/2001 | Harris |
| 6,312,725 B1 | 11/2001 | Wallace et al. |
| 6,371,975 B2 | 4/2002 | Cruise et al. |
| 6,458,889 B1 | 10/2002 | Trollsas et al. |
| 6,465,001 B1 | 10/2002 | Hubbell et al. |
| 6,503,731 B2 | 1/2003 | Marx et al. |
| 2004/0076602 A1 | 4/2004 | Harris |

FOREIGN PATENT DOCUMENTS

| | | | |
|---|---|---|---|
| WO | 94/03155 A1 | 2/1994 | |
| WO | 94/13311 A1 | 6/1994 | |
| WO | 96/03159 A1 | 2/1996 | |
| WO | WO 9617871 A1 * | 6/1996 | |
| WO | 97/22371 A1 | 6/1997 | |
| WO | 99/22770 A1 | 1/1998 | |
| WO | 98/35631 A1 | 8/1998 | |
| WO | 99/10022 A3 | 3/1999 | |
| WO | 99/14259 A1 | 3/1999 | |
| WO | 99/34833 A1 | 7/1999 | |
| WO | 00/12018 A1 | 3/2000 | |
| WO | 00/72852 A1 | 12/2000 | |

OTHER PUBLICATIONS

Baines et al., "Adsorption and Removal of Protein Bound to Hydrogel Contact Lenses," Optom Vis Sci 67:807-810 (1990) (abstract).
Bick, "Hemostasis Defects," Seminars in Thrombosis and Hemostasis 11:263-264 (1985).
Bick, "Physiology and Pathophysiology of Hemostasis During Cardiac Surgery" (excerpts), 1995.
Bite et al., "Macrosorb Kieselguhr-Agarose Composite Adsorbents. New Tools for Downstream Process Design and Scale Up. Scientific Note," Appl Biochem Biotechnol 18:275-284 (1988) (abstract).
Burczak et al., "Protein Permeation Through Poly(Vinyl Alcohol) Hydrogel Membranes," Biornateria/s 15:231-238 (1994) (abstract).
Burgi, "A Simple Method for the Concentration of Protein for Electrophoresis of Urine and Cerebrospinal Fluid," Z Kim Chem Kim Biochem 5:277 (1967) (abstract).
Garrett et al, "Human Serum Albumin Adsorption on Hydrogel Contact Lenses In Vitro," Invest Aphtha/mol Vis Sci 37:2594-2602 (1996) (abstract).
Gayet et al, "High Water Content BSA-PEG Hydrogel for Controlled Release Device: Evaluation of the Drug Release Properties", Journal of Controlled Release, 38:177-184 (1996).
Irwin et al., "The Effect of Cyclodextrins on the Stability of Peptides in Nasal Enzymic Systems" Pharmaceutical Research, 11(12):1968-1703(1994).
Keller et al., "Determination of the Protein Concentration in the Cerebrospinal Fluid. Criticism of the Methods," Med Welt 23:1319-1325 (1969) (abstract).
Keogh et al., "Albumin binding surfaces for biomaterials", Laboratory and Clinical Medicine, 124.4:537-545 (1994).
Kissel et al., "Parenteral depot-systems on the basis of biodegradable polyesters", J of Controlled Release 16:27-42 (1991).
Kissel et al. "ABA-triblock Copolymers from Biodegradable Polyester A-blocks and Hydrophilic Poly(ethylene ) xide) B-Blocks as a Candidate for In Situ Forming Hydrogel Delivery Systems for Proteins" Advanced Drug Delivery Reviews, 54:99-134 (2002).
Kluge et al., "Results of Comparisons of Various Methods of Determining Total Cerebrospinal Fluid Protein," Dtsch Gesundheitsw 23:2039-2041(1968) (abstract).
Kolthammer, "The In Vitro Adsorption of Drugs from Horse Serum onto Carbon Coated with an Acrylic Hydrogel," JPhari'n Pharrnaco/ 27:801-805 (1975) (abstract).
Kulik et al., "In Vitro Platelet Adhesion to Nonionic and Ionic Hydrogels with Different Water Contents," J Biomed Mater Res 30:295-304 (1996) (abstract).
Lazarus et al., "Selective In Vivo Removal of Rheumatoid Factor by an Extracorporeal Treatment Device in Rheumatoid Arthritis Patients," Transfusion 31:122-128 (1991) (abstract).
Lin et al., "The Influence of Adsorption of Native and Modified Antibodies on Their Activity," J Imrnunol Methods 125:67-77 (1989) (abstract).
Mathiowitz et al., "Polyanhydride Microspheres as Drug Carriers I. Hot-Melt Microencapsulation", J Controlled Release 5:13-22 (1987).
Molina et al., "Protein Release from Physically Crosslinked Hydrogels of the PLA/PEO/PLA Triblock Copolymer-type", Biomaterials, 22:363-369 (2001).
Nihant et al., "Polylactide Microparticles Prepared by Double Emulsion-Evaporation", J. Colloid & Interface Science 173:55-65 (1995).
Pathak et al., "Rapid Photopolymerization of Immunoprotective Gels in Contact with Cells and Tissue", J Am Chem. Soc., 114, 8311-8312 (1992).
Reddi et al., "Polyurethane Microspheres as Drug Carriers", Macromolecular Reports A32:789-799 (1995).
Saraydin et al., "Adsorption of Bovine Serum Albumin onto Acrylamide-Maleic Acid Hydrogels," Biomaterials 15:917-920 (1994) (abstract).

(56) References Cited

OTHER PUBLICATIONS

Sawhney et al., "Bioerodible Hydrogels Based on Photopholmerized Poly(ethylene glycol)-co-poly($\alpha$-hydroxy acid) Diacrylate Macromers", Macromolecules 26:581-587 (1993).
Schlag et al., "Fribin Sealant in Orthopedic Surgery" Fibrin Sealant in Operative Orthopedic Surgery vol. 1-7:269-284 (1986).
Sierra et al., "A Method to determine Shear Adhesive Strength of Fibrin Sealants," Journal of Applied Biomaterials, 3:147-151 (1992).
Sierra, "Fibrin Sealant Adhesive Systems: A Review of Their Chemistry, Material Properties and Clinical Applications," Journal of Biomaterials Applications 7:309-352 (1993).
Silver et al., "Effect of Protein Adsorption on the Blood-Contacting Response of Sulphonated Polyurethanes," Biomaterials 14:834-844 (1993) (abstract).
Smith et al., "Thrombin and Albumin Adsorption to PV A and Heparin-PV A Hydrogels. 2: Competition and Displacement," J Biomed Mater Res 27:89-95 (1993) (abstract).
Tabata et al., "Controlled Delivery Systems for Proteins Using Polyanhydride Microspheres" Pharmaceutical Research, 10(4):487-496 (1993).
Vermes, "Cerebrospinal Fluid Proteins: I, Comparative Study of Concentration Methods," Arq Neuropsiquiatr 41:1-8 (1983) (abstract).
Walther et al., "Pore-Size Distributions of Cationic Polyacrylamide Hydrogels of Different Compositions Maintained at the Same Swelling Capacity", J. Macromol. Sci.-Phys. B33 (3&4):267-286 (1994).
Wang et al, "Hydrogels as Separation Agents," Advances in Polymer Science 110:67-79 (1993).

\* cited by examiner

METHODS FOR PREPARATION OF PLATELET RICH PLASMA

CROSS-REFERENCE TO RELATED APPLICATIONS

This application is a continuation of U.S. application Ser. No. 11/725,751 filed on Mar. 20, 2007, now U.S. Pat. No. 7,605,232, entitled "Hydrogels for Protein Concentration", which is a continuation of Ser. No. 10/293,453 filed on Nov. 13, 2002, now U.S. Pat. No. 7,211,651, entitled "Proteinaceous Gels Having Visualization Agents and Methods of Use Thereof", which is a continuation of U.S. application Ser. No. 10/068,807 filed on Feb. 5, 2002, now U.S. Pat. No. 6,887,974, entitled "Crosslinking Agents and Methods of Use" which is a divisional of U.S. application Ser. No. 09/147,897 filed Aug. 30, 1999 (abandoned) entitled "Methods and Devices for Preparing Protein Concentrates" filed under U.S.C. §3.71 with priority to International Application No. PCT/US97/16897 filed Sep. 22, 1997, which claims priority to U.S. application Ser. No. 60/026,526 filed Sep. 23, 1996; U.S. application Ser. No. 60/039,904 filed Mar. 4, 1997 and U.S. application Ser. No. 60/040,417 filed Mar. 13, 1997, the disclosures of which are herein incorporated by reference.

INTRODUCTION

1. Technical Field

The field of the invention relates to materials for use in a patient, particularly to fibrin adhesive systems.

2. Background of the Invention

Methods of preparing concentrated protein compositions from initial dilute protein compositions find use in a variety of different industries, including the chemical, biological, academic research, biotechnological and medical industries. For example, "Fibrin Sealants" (also known as fibrin gels or fibrin glues) are a type of blood derived composition used in the medical industry which are prepared through methods of concentrating blood plasma proteins that have been developed for use as tissue adhesives, drug delivery vehicles and the like. Although such compositions are not yet FDA approved in the United States due to concerns over blood borne contaminants, such compositions are marketed in Europe and elsewhere throughout the world. A typical commercial fibrin glue kit consists of a vial of lyophilized concentrated human fibrinogen, prepared from pooled human donor blood, that also contains fibronectin, Factor XIII and reduced amounts of plasminogen. The concentrate, also known as cryoprecipitate, is reconstituted with a reconstituting solution and warmed to 37° C. The second component of the adhesive system is a lyophilized bovine thrombin solution which is reconstituted with a calcium chloride solution. The formulation may also contain additional components like a fibrionolysis inhibitor. The reconstituted solutions are mixed and used as a surgical adhesive system.

The most common method used for the preparation of the fibrinogen component of the above described kits is cryoprecipitation. In cryoprecipitation, fresh blood plasma is frozen at −80° C. for at least 6 to 12 h. The temperature of the frozen plasma is then raised to around 0-4° C., resulting in the formation of a precipitated supernatant that contains fibrinogen and Factor XIII, i.e. a cryoprecipitate. The cryoprecipitated suspension is then recovered. Another method described in the literature is the use of common non-toxic organic/inorganic compounds such as ethanol, polyethylene glycol, poly(vinyl alcohol), 1-6-hexanoic acid and ammonium sulfate as precipitating agents.

The above methods of preparing the fibrinogen containing component of fibrin glue compositions are time consuming and complex. Furthermore, in approaches such as cryoprecipitation, special equipment like a refrigerated centrifuge, is often required. Finally, different methods of precipitation produce fractions with different adhesive and physical characteristics which can adversely affect the ultimate adhesive product.

Accordingly, there is a continued need for the development of new methods for preparing concentrated protein compositions, and particularly fibrinogen rich fractions from blood compositions. Ideally, such methods would: be relatively simple and rapid; require minimal handling of the plasma and not include a cryoprecipitation step; and provide serum concentrates suitable for use in fibrin glue systems, in wound healing promotion systems, in drug delivery, and in tissue regeneration. Furthermore, such methods would ideally be suitable for use in the preparation of autologous serum concentrates that eliminate pathogen transmission risk present in serum concentrates prepared from pooled donor sources. Also of interest would be the development of a simple method capable of efficiently producing concentrated protein compositions from large volumes of initial fluid, e.g. pooled human serum in emergency surgery situations. Also of interest would be the development of devices for use in performing the subject methods.

RELEVANT LITERATURE

Fibrin sealants and methods for their production, as well as clinical applications thereof, are reviewed in David H. Sierra, "Fibrin Sealant Adhesive Systems: A Review of Their Chemistry, Material Properties and Clinical Applications," J. Biomaterials Applications (1993) 7:309-352. Other references of interest include: Sierra & Feldman, J. Applied Biomaterials (1992) 3:147-151; U.S. Pat. Nos. 5,405,607; 5,030,215; and 5,395,923.

Devices for preparing and administering a fibrin sealant to facilitate tissue repair are described in: U.S. Pat. Nos. 4,874,368; 4,631,055; 4,735,616; 4,359,049; 4,978,336; 5,116,315; 4,902,281; 4,932,942; WO 91/09641, and Tange, R. A., Fibrin Sealant in Operative Medicine: Otolaryngology—Vol. 1 (1986).

Microencapsulated drug particles and similarly protected pharmaceutically active agents are described in: Kissel et al., J. Controlled Release (1991) 16:27; Tabata et al., Pharmaceutical Research (1993) 10:487; EPA 83303606.4; U.S. Pat. No. 5,143,662; Mathiowitz & Langer, J. Controlled Release (1987) 5:13; Nihant et al., J. Colloid & Interface Science (1995) 173:55; and Irwin et al., Pharmaceutical Research (1994) 11:1968.

Hydrogels and methods for their preparation are reported in: U.S. Pat. Nos. 5,626,863; 5,573,934; 5,567,435; 5,410,016; 5,529,914; 5,514,380; 5,476,909; 5,041,292, 5,583,114; as well as in Walter et al., J. Macromol. Sci.-Phys. (1994) B33 (3&4):267; Pathak et al., J. Am. Chem. Soc. (1992) 114:8311; Sawhney et al., Macromolecules (1993) 26:581; Keogh & Eaton, J. Laboratory & Clinical Med. (1994) 124:4:537; and Reddi et al., Macromolecular Reports (1995) A32:789.

SUMMARY OF THE INVENTION

Methods and devices for the preparation of protein concentrates, as well as novel protein concentrate compositions prepared thereby, products derived therefrom and applications in which the products find use, are provided. In the subject methods, an initial protein comprising composition, such as whole blood or plasma, is contacted with a non-protein denaturant hydrogel under conditions sufficient for a substantial portion of the water present in the initial composition to be absorbed by the hydrogel. Following absorption, the resultant protein rich phase is separated from the swollen hydrogel phase to produce the protein concentrate. The subject methods find use in a variety of applications, particularly in the preparation of fibrinogen rich compositions from whole blood or derivatives thereof, where the resultant fibrinogen compositions find use in a variety of applications, as fibrin sealant tissue adhesives, as drug delivery vehicles, as sources of growth factors to promote wound healing, and the like.

DESCRIPTION OF THE SPECIFIC EMBODIMENTS

Figure 1A:
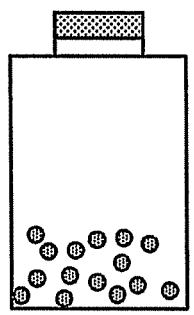
FIG. 1A provides a schematic representation of the inventive method of preparing fibrinogen rich compositions.

Methods and devices for the preparation of protein concentrates, as well as novel protein concentrate compositions prepared thereby and products derived therefrom, are provided. In the subject methods, an initial protein comprising composition, such as whole blood or plasma, is contacted with a non-protein denaturant hydrogel under conditions sufficient for a substantial portion of the water present in the initial composition to be absorbed by the hydrogel. Following absorption, the resultant protein rich phase is removed from the swollen hydrogel to produce the protein concentrate, where the term "removed" is employed in a broad sense to mean that the swollen hydrogel and the protein rich phase are isolated from one another, where removal can be accomplished via active separation, e.g. by centrifugation, or passively, e.g. in those embodiments where the hydrogel and protein rich phase separate by themselves, where the protein rich phase is subsequently isolated from the hydrogel through simple aspiration or other analogous technique. By selecting an appropriate hydrogel, the nature of the resultant protein concentrate may be controlled. The subject methods find use in a variety of applications, particularly in the preparation of fibrinogen rich compositions from whole blood or derivatives thereof (where the initial blood composition may be a pooled donor source or an autologous source, where the resultant fibrinogen compositions find use in a variety of applications, fibrin sealant tissue adhesives, drug delivery vehicles, and the like. In further describing the subject invention, the methods for preparing the subject protein concentrates will first be described in greater detail, followed by a discussion of the resultant concentrates themselves, representative applications in which they find use and kits and devices suitable for use in their preparation.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

In practicing the subject methods, an initial protein comprising composition is contacted with a hydrogel under conditions sufficient for at least a portion of at least the water present in said blood composition to be absorbed by the hydrogel. The initial protein containing composition may be any aqueous composition that comprises one or more proteins of interest, where such compositions include both naturally occurring compositions, such as physiologically derived fluids, e.g. blood, plasma, urine, cerebrospinal fluid, tears, saliva, milk, peritoneal cavity fluid and the like; and synthetically prepared compositions, e.g. tissue culture medium, and the like. Physiological fluids of interest may be obtained from a variety of hosts, including cows, sheep, pigs, deer, humans and the like. For example, the subject methods can be used to produce enriched protein compositions from cow or sheep milk, where the cow or sheep may be a transgenic animal engineered to produce milk containing a recombinant protein of interest.

Of particular interest is the preparation of protein concentrates from initial blood compositions. The blood composition employed in the subject methods will typically be derived from a mammalian source, where suitable sources include cows, sheep, pigs, deer, humans and the like, where humans may be the preferred source depending on the intended use of the composition. The blood composition may be whole blood or a blood product, i.e. a whole blood derivative, where whole blood is subjected to one or more filtration steps, e.g. removal of red blood cells, and the like. In other words, blood compositions that may be used in the subject invention include both whole blood and blood derivatives, e.g. plasma, platelet containing serum, and the like, where such blood compositions may be obtained from their hosts and produced according to methods known in the art. The blood composition, prior to use, may be screened for the presence of one more pathogens, e.g. AIDS, Hepatitis B, etc. One or more components may be added to the blood composition, such as anticoagulants, and the like. The blood composition may be derived from a pooled supply of blood from a variety of different hosts, i.e. a pooled donor supply, or from the host in which the ultimate protein concentrate is to be employed, i.e. an autologous source.

For clarity and ease of understanding, the invention is further described below in terms of the preparation of a protein concentrate, e.g. a fibrinogen rich composition, from an initial blood composition as described above. However, in so describing the invention, it should be understood that the full scope of the invention also encompasses the preparation of protein concentrates from non-blood compositions, as described above.

The hydrogel with which the blood composition is combined in the subject methods may comprise one or more different hydrogels in combination, where usually no more than four different hydrogels, and more usually no more than three hydrogels will be used together, where a combination of different hydrogels may be employed for greater control over the types of components of the blood composition that are absorbed by the hydrogel and the nature of the resultant fibrinogen rich composition. For example, a hydrogel blend may be employed that combines a hydrogel with a first particular cut-off value, as described in greater detail below, and a second hydrogel that selectively removes a particular component of the initial fluid, e.g. albumin. Hydrogels employed in the subject methods are compositions that are capable of absorbing water from an aqueous composition with which they are contacted to swell in size and increase in mass, where the increase in mass will typically be at least 10 and up to 1000 fold or greater than the dry mass of the hydrogel. Importantly, the hydrogels will be hydrogels which do not denature or modulate the conformation of proteins with which they come into contact, i.e. the hydrogels employed in the subject invention are non-protein denaturant hydrogels. Preferred are hydrogels that are highly resistant to protein adsorption.

Hydrogels suitable for use in the subject methods will be biocompatible, by which is meant that they are suitable for contact with a blood derived composition that is to be introduced into a mammalian host, i.e. they will not leach toxic or unwanted substances into the blood composition upon contact. Preferably, the hydrogel will be one that does not substantially change the pH of the blood composition with which it is contacted and is sterile in nature.

Suitable hydrogels include macromolecular and polymeric materials into which water and small molecules can easily diffuse and include hydrogels prepared through the cross linking, where crosslinking may be either through covalent, ionic or hydrophobic bonds introduced through use of either chemical cross-linking agents or electromagnetic radiation, such as ultraviolet light, of both natural and synthetic hydrophilic polymers, including homo and co-polymers. Hydrogels of interest include those prepared through the cross-linking of: polyethers, e.g. polyakyleneoxides such as poly (ethylene glycol), poly(ethylene oxide), poly(ethylene oxide)-co-(poly(propyleneoxide) block copolymers; poly(vinyl alcohol); poly(vinyl pyrrolidone); polysaccharides, e.g. hyaluronic acid, dextran, chondroitin sulfate, heparin, heparin sulfate or alginate; proteins, e.g. gelatin, collagen, albumin, ovalbumin or polyamino acids; and the like. Because of their high degree of biocompatibility and resistance to protein adsorption, polyether derived hydrogels are preferred, with poly(ethylene glycol) derived hydrogels being particularly preferred.

Physical characteristics such as size, shape and surface area can affect the absorption characteristics of the hydrogel composition. Accordingly, the hydrogel composition that is employed may be in a variety of configurations, including particles, beads, rods, sheets, irregular shapes and the like, where those shapes with greater surface area to total mass ratios are preferred, at least in certain embodiments. The porosity of the hydrogel, which is dependent on the amount or degree of crosslinking present in the hydrogel, also affects the absorption characteristics of the hydrogel. For example, where absorption of water and small molecules is desired, a hydrogel with a high degree of crosslinking and a consequent small average porosity will be employed. Conversely, where the selective absorption of small proteins is also desired, a hydrogel with a low degree of crosslinking and a consequent large average porosity will be employed. Of interest for certain embodiments of the subject invention, e.g. where the selective removal of albumin and other components of similar or lower molecular weight is desired, are hydrogels that have a molecular weight "cut-off" absorption point (i.e. a molecular weight limitation in excess of which components are not absorbed) of about 80,000 daltons. Other hydrogels of particular interest are for use in certain embodiments are those having molecular weight cutoffs of: 100,000 daltons (where one desires to retain immunoglobulins); 150,000 daltons (where the removal of immunoglobulins is desired); 15,000 daltons (where one desires to retain growth factors in the protein concentrate); etc.

To further tailor the absorptive properties of the hydrogel, the hydrogel can be modified to provide for specific binding of one or more of the components of the blood composition to the surface of the hydrogel. For example, where the selective absorption of albumin in addition to water is desired, the hydrogel can be modified to comprise an albumin specific binding reagent, such as Cibacron blue, as described in Keogh & Eaton, J. Lab. & Clin. Med. (1994) 124:537. Other means of tailoring the hyrdogels to further control the nature of the protein concentrate produced by the subject method include using hydrogels comprising agents that act as water absorbents and/or precipitants, where such agents include ethanol, PEG 400, phosphate buffer and the like.

The hydrogel compositions employed in the subject methods can be prepared by methods known to those skilled in the art, where specific methods for producing a number of different hydrogels which are suitable for use in the subject can be found in the Experimental Section infra. Alternatively, suitable hydrogels or precursors thereof may be purchased from various commercial sources, where such sources include: Shearwater, BASF, Polysciences and the like.

Specific hydrogels suitable for use in the subject methods are described in U.S. Pat. Nos. 5,626,863; 5,573,934; 5,567,435; 5,529,914; 5,514,380; 5,476,909; 5,041,292, the disclosures of which are herein incorporated by reference. Of particular interest in many embodiments of the subject invention are the hydrogels described in U.S. Pat. No. 5,410,016, the disclosure of which is herein incorporated by interest. Specific hydrogels of interest include: cross-linked poly(ethylene glycol diacrylate); cross-linked poly(ethylene oxide)-(polypropylene oxide)-poly(ethylene oxide) diacrylate; and the like.

The blood composition is contacted with the hydrogel under conditions sufficient for at least some of, and in many cases a substantial amount of, at least the water component of the blood composition to be absorbed from the blood composition into the hydrogel to produce a fibrinogen rich composition and a swollen hydrogel. By substantial amount of water is meant at least about 10%, usually at least about 50% and more usually at least about 90%-95% of the initial water present in the blood composition. Any convenient means of contacting the blood composition with the hydrogel may be employed, such as placing both components into the same container, mixing or agitating the two components to combine them, and the like. The amount of hydrogel that is contacted with the blood composition will be sufficient to absorb the desired amount of water and other components from the blood composition. Where a dry hydrogel composition is employed, 1 gram of dry hydrogel material will be used for fluid volume ranging from about 5 to 200 ml, usually from about 10 to 150 ml. For a partially hydrated hydrogel composition (where partially hydrated means a hydrogel composition comprising from about 20 to 50% polymer), one gram of hydrogel will be used for a volume of fluid ranging from about 1 to 10 ml, usually from about 2 to 3 ml. The two components will be maintained in contact for sufficient time for the desired amount of water (as well as other desired components) to be absorbed by the hydrogel. The amount of time for which contact is maintained between the hydrogel and the composition will vary depending on the particular nature of the hydrogel, i.e. composition, degree of hydration and surface area. For example, a longer period of time may be required when partially hydrated hydrogels are employed, where a shorter period of time may be sufficient when completely dehydrated and/or an excess of hydrogel is employed. Usually contact will be maintained for at least about 30 min and will generally not be maintained for more than 200 hours, where embodiments in which contact does not have to be maintained for more than about 48 hours are preferred. In the mixture (i.e. absorption mixture) into which the two components are combined in the contacting step, the pH will be maintained at from 6.5 to 11, usually from about 6.5 to 7.5 and more usually from about 7 to 7.5. The temperature of the absorption mixture will be maintained at from about 0 to 40, usually from about 0 to 30 and more usually from about 4 to 30° C. c In addition to the blood composition and hydrogel, the absorption mixture may further comprise one or more additional agents which serve a variety of purposes. Such agents include: anticoagulants, such as heparin, buffering agents, e.g. citrate buffer, HEPES, and the like.

Absorption of water and other components, as described above, by the hydrogel in the absorption mixture results in the production of a fibrinogen rich phase and a swollen hydrogel. The resultant volume of protein concentrate, e.g. fibrinogen rich phase, will usually be less than 0.5, usually less than about 0.25 and more usually less than about 0.1 of the initial protein comprising composition.

The subject methods of preparing protein concentrate compositions may be used in conjunction with one or more additional protein concentration and/or separation techniques, e.g. chromatography, precipitation with a precipitation agent, and the like, where such methods are known to those of skill in the art. In certain embodiments of the subject invention, the process may further comprise the addition of one or more additional volumes of water to the protein concentrate following the initial absorption of water and components from the initial fluid. For example, a first volume of serum could be contacted with a hydrogel and reduced to 0.1 of its initial volume following absorption of water by the hydrogel. A volume of water could then be added to the reduced volume and absorption be allowed to occur for a second time, whereby further components are removed from the concentrate. This process could be repeated a plurality of times, as desired.

The fibrinogen rich phase is then removed from the swollen hydrogel to yield the subject fibrinogen rich composition. Removal of the fibrinogen rich phase from the swollen hydrogel may be performed using any convenient technique or protocol. For example, the fibrinogen rich may be removed from the swollen hydrogel by aspirating the fibrinogen rich phase from the hydrogel surface. Alternatively, the fibrinogen rich phase may be removed from the swollen hydrogel through centrifugation, which separates the two phases. Other techniques that may be employed include: decanting, filtration, simple mechanical separation, and the like.

The above process may be repeated one or more additional times to obtain a final protein rich composition of desired characteristics.

Separation yields a fibrinogen rich composition. The fibrinogen rich composition, because of the method by which it is produced, will be more concentrated in protein than the initial composition, where in certain embodiments the total protein concentration will be about 10 times greater, and in many embodiments the total protein concentration will be about 5 to 9 times greater than the protein concentration of the initial composition. The concentration of fibrinogen in the fibrinogen rich composition will range from about 1 to 100, usually from about 1 to 30 and more usually from about 1 to 2 mg/ml, where in those embodiments in which the fibrinogen rich composition is to be employed in a fibrin glue system, the fibrinogen concentration will range from about 30 to 60 mg/ml.

Depending on the particular nature of the hydrogel system employed, the resultant fibrinogen rich compositions may be substantially free of one or more low molecular weight components naturally present in the initial blood composition, such as albumin, growth factors, and the like. For example, where hydrogels with a molecular weight cutoff, as described above, of 100,000 daltons are employed, the resultant fibrinogen rich compositions will be substantially free of components having a weight that does not exceed 100,000 daltons. Of particular interest in certain embodiments is the preparation of fibrinogen rich compositions with reduced albumin concentration, i.e. compositions that have reduced albumin concentrations over that which would occur during the concentration process.

The subject fibrinogen rich composition may be used as produced above or modified through the addition of one or more different agents that modulate the chemical and/or physical nature of the composition. Additional agents which may added to the composition include: proteins associated with coagulation, e.g. Factor II, fibronectin and the like; viscosity modifiers, such as collagen, sodium hyaluronate, and the like; antioxidants, such as hydroquinone, vitamin E, and the like; buffering agents, such as HEPES and the like; processing aids, antifibrinolytic agents, platelet activating agents, wound healing agents, and the like. Of particular interest in certain embodiments of the invention, particularly where the composition is to be used in a firbin sealant tissue adhesive, is the modification of the fibrinogen rich composition to comprise a visualization agent. Visualization agents (i.e. agents that may help a surgeon see those tissues to which the fibrin glue has been applied) that find use include blood compatible, non-toxic flourescent compounds and chromogenic dyes, where specific visualization agents of interest are those that provide for color contrast with the background tissue, with blue and green being preferred colors, where specific agents include: indocyanine green, FD & C no. 1, FD & C no. 6, eosin, fluorescein, and the like.

Following preparation of the fibrinogen rich composition, the composition may be used immediately or stored for use at a subsequent time. Any suitable storage means may be employed, where the storage means will typically be sterile where the composition is to ultimately be used in a physiological setting, e.g. where it is to be used in a drug delivery vehicle, as a surgical adhesive and the like, as further described below. One convenient means of storing the composition is to lyophilize the composition and package the lyophilized product in a sterile packaging for subsequent use, such as a syringe. Alternatively, the composition may be stored at a reduced temperature, e.g. from about 4 to −20° C. or lower.

The subject method of preparing the fibrinogen rich composition may be performed at both the laboratory scale and scaled up to produce large amounts of fibrinogen rich composition, e.g from pooled plasma. On the laboratory scale, the process of the invention may be conducted using standard laboratory and medical equipment. For example, whole blood may be withdrawn from a mammalian host into a syringe containing an anticoagulant and emptied into a sterile centrifuge tube containing the absorbable hydrogel, e.g. hydrogel beads. The hydrogel is then allowed to swell in the presence of whole blood for a period of time sufficient for the desired amount of protein concentration to occur, as described above. The resultant concentrated plasma, i.e. fibrinogen rich phase, is then separated from swollen hydrogel and other cellular material, e.g. red blood cells, by any convenient means, e.g. centrifugation and aspiration using a blunt needle. Such laboratory scale processes find particular use in situations where one wishes to prepare an autologous tissue adhesive, e.g. where the adhesive is prepared from a patient's own blood prior to, or even during, a surgical operation. For scale-up preparation from large volumes of initial blood composition, pooled blood plasma, which may be screened for viruses such as Hepatitis B, and AIDS, may be transferred to a batch reactor containing sterile absorbable hydrogel beads, e.g. photo polymerized polyethylene glycol diacrylate (molecular weight range 20,000 daltons), and the like. The beads may then be allowed to absorb water present in the pooled plasma until a desired level of fibrinogen concentration is reached. After reaching the fibrinogen level (typically >30 mg/ml), the beads are separated from the concentrated solution, i.e. fibrinogen rich composition, either by filtration, centrifugation, or through their settling out due to gravity.

The subject fibrinogen rich compositions find use in a variety of applications, as components of tissue adhesives, in drug delivery vehicles, hemostatic agents, wound healing agents, and the like. In tissue adhesives, the subject compositions will be used in combination with a coagulation component, usually a solution of thrombin and calcium ions, where upon combination of the composition with the coagulation component a fibrin sealant composition is produced which sets into a biocompatible proteinaceous matrix, i.e. a fibrin gel or sealant. A variety of different methodologies and devices for performing such methodologies have been developed for preparing fibrin sealants from fibrinogen rich compositions, and such methodologies and techniques are suitable to prepare a fibrin sealant from the subject compositions. As with the preparation of fibrin sealants from fibrinogen compositions prepared from prior art methods, fibrin sealants may be prepared from the subject compositions by applying them to a tissue repair site (i.e. a tissue site to which adherence of a second tissue is desired) either simultaneously or sequentially with a thrombin/calcium ion setting composition, where suitable thrombin/calcium compositions are readily available from commercial sources and known to those of skill in the art. To apply the fibrin sealant, the two components described above may simply be applied sequentially or simultaneously to the tissue repair site via a needle or syringe or other application system. In certain embodiments, it is preferred to apply the components sequentially so as to "prime" the tissue, which results in improved tissue adhesive results. Where the tissue is primed, a first component of the fibrin glue, e.g. the crosslinker or thrombin, is applied to the tissue repair site. Next, the fibrinogen components, which may include additional crosslinker/thrombin, is applied. Instead of manually applying the fibrin glue to the tissue repair site, one may use specialized devices for applying the two components of the fibrin glue. Representative devices which may be used include those described in U.S. Pat. Nos. 4,874,368; 4,631,055; 4,735,616; 4,359,049; 4,978,336; 5,116,315; 4,902,281; 4,932,942; WO 91/09641, and Tange, R. A., Fibrin Sealant in Operative Medicine: Otolaryngology—Vol. 1 (1986), the disclosures of which are herein incorporated by reference.

Fibrin sealants as prepared above with subject compositions find use as tissue adhesives in a variety of clinical applications, where such applications are reviewed in Schlag & Redl, Fibrin Sealant in Operative Surgery (1986) Vol. 1-7, and include: cardiovascular surgery, orthopaedic surgery, neurosurgery, ophthalmic surgery, general surgery and traumatology, plastic reconstruction and maxillofacial surgery, otorhinolaryngology, and the like. Where convenient, the fibrin sealant may comprise a visualization agent (e.g. where the sealant is used in a laproscopic method). The visualization agent, including those described above, may be present in one or both of, but usually one of, the components of the fibrin sealant, i.e. it may be present in the fibrinogen rich component (where it may have been introduced to the fibrinogen rich composition after its production or introduced into the initial fluid from which the fibrinogen rich compositions is produced (with the amount used selected in view of the absorption of agent by the hydrogel)) and/or the thrombin/calcium ion component.

The subject fibrinogen rich compositions according to the subject invention may also be used in a fibrin gel or sealant or matrix for biologically active agent or drug delivery. Active agents of interest which may be delivered with fibrin sealant compositions prepared as described above include: proteins, carbohydrates, nucleic acids, and inorganic and organic biologically active molecules, where specific biologically active agents include but are not limited to: enzymes, antibiotics, antineoplastic agents, local anesthetics, hormones, antiangiogenic agents, antibodies, neurotransmitters, psychoactive drugs, drugs affecting reproductive organs, and oligoncucleotides such as antisense oligonucleotides. To prepare fibrin sealant drug delivery compositions with the subject fibrinogen rich compositions, one may simply combine a therapeutically effective amount of the active agent with one or both of the components of the fibrin sealant and prepare the sealant as described above.

In a preferred embodiment of the subject invention, the active agent or agents are present in a separate phase from the fibrin gel which protects the fibrin gel while it is setting from adverse effects of the active agent and/or modulates the release kinetics of the active agent from the gel, where "separate phase" could be: oil (oil-in-water emulsion); biodegradable vehicle; and the like. Biodegradable vehicles in which the active agent may be present include: encapsulation vehicles, such as microparticles, microspheres, microbeads, micropellets and the like, where the active agent is encapsulated in a bioerodible or biodegradable polymer such as: polyanhydride, polyglycolic acid, polylactic acid, polyorthocarbonate, polycaprolactone, polytrimethylene carbonate or their copolymers; caging or entrapping molecules, such as cyclodextrins and the like, etc. Biodegradeable vehicle protected active agents are particularly preferred where the active agent is an antibiotic, such as gentamycin, tetracylcine, and the like.

In using fibrin sealants prepared from the subject fibrinogen rich compositions as drug delivery vehicles, the fibrin sealant comprising the active agent, where the agent may be originally present in the fibrinogen and/or thrombin component of the sealant gel, which is optionally and preferably present in a biodegradable vehicle, will be administered to a host prior to setting of the fibrin sealant or gel, where upon administration the gel will set and act as a depot for release of the active agent to the host. Such methods of drug delivery find use in both systemic and local administration of an active agent. In using the fibrin sealants for drug delivery as described above, the amount of fibrin sealant and dosage of agent introduced into the host will necessarily depend upon the particular drug and condition being treated. Administration may be by any convenient means, such as syringe, cannula, trochar, and the like.

While various illustrative uses of the fibrinogen rich compositions prepared by the subject methods have been reviewed above, as explained supra the subject methods are not limited to the preparation of fibrinogen rich compositions, but can be used to produce other protein concentrates. For example, by selecting the appropriate hydrogel with the appropriate absorptive properties, one can prepare albumin rich compositions.

Albumin rich compositions can be used in the preparation of albumin tissue adhesives or glues analogous to fibrin glues. For albumin glues, the albumin present in the albumin rich phase can be crosslinked using a number of different crosslinking means, including the use of chemical crosslinking agents, such as polyaldehydes, thermal crosslinking agents, such indocyanine green in combination with light (e.g. laser emitting at 780 nm), and the like. See U.S. Pat. No. 5,583,114, the disclosure of which is herein incorporated by reference.

In certain embodiments of the invention, a water soluble, biodegradeable synthetic cross-linkers will find use in the preparation of protein gels, such as fibrin glues and albumin glues mentioned above, or other compositions in which polymeric compounds are cross-linked, as described herein and in other applications known to those of skill in the art. The water soluble, biodegradeable synthetic cross-linkers will be multifunctional, where by multifunctional is meant that the cross-linkers will be other than monofunctional, where illustrative multifunctional cross-linkers are difunctional, trifunctional, tetrafunctional, pentafunctional, hexafunctional . . . up to "n"-functional, where n is an integer representing the number of different end cap functional regions present on the polymeric crosslinkers.

The water soluble, biodegradable polymeric crosslinkers will have a core that is a biologically inert polymeric unit; (b) an extension at each end of the core that is a biodegradable polymeric unit; and (c) an end cap on each extension that is a reactive moiety.

The biologically inert polymeric unit or region that makes up the core of the compound will be an inert polymeric block that is biocompatible, where the block may or may not be biodegradable. Preferably, the core is a polymeric region that is water soluble, where preferred polymers from which the core may be derived include: polyethers, e.g. polyakyleneoxides such as poly(ethylene glycol), poly(ethylene oxide), poly(ethylene oxide)-co-(poly(propyleneoxide)block copolymers; poly(vinyl alcohol); poly(vinyl pyrrolidone), poly (amino acids), poly(ethyloxzoline), dextran and the like, where polyethers, and more particularly polyoxyalkylenes, are preferred.

The biodegradable extension component of the subject crosslinkers will be a component that degrades under physiological conditions into non-toxic products, where the biodegradable extension component will generally be hydrolyzable. Hydrolyzable components of interest include: polymers, copolymers and oligomers of: glycolide, dl-lacide, d-lactide, l-lactide, caprolactone, dioxanone and trimethylene carbonate or their copolymers and the like. In many instances it is desirable to have polylinkers with enzymatically hydrolyzable biodegradable extension components, e.g. regions cleavable by metalloproteinases and collagenases, where such components will generally be peptidic. Illustrative biodegradable regions include: polyhydroxyacids, polyorthocarbonates, polyanhydrides, polylactones, polyaminoacids and polyphosphates and the like. The size or length of biodegradable region may be varied to in a number of ways. For example, by using a crosslinker based on glycolide in the crosslinking of proteins, the resultant crosslinked protein degrades much faster than crosslinked proteins based on polycaprolactone cross-linkers. Thus, by choosing appropriate biodegradable polymer regions in the crosslinker, a suitable degradation profile of the resultant crosslinked protein can be obtained. With difunctional cross-linkers, peptidic biodegradable regions are preferred.

The reactive moiety that is the end-cap on each of the extensions is an activated functional group which provides for covalent bonding to proteins under in vivo conditions without free radical initiation. Such groups include carbodiimidazole, sulfonyl chloride, chlorocarbonates, n-hydroxysuccinimdyl ester, succinimidyl ester, epoxides, aryl halides, sulfasuccinimidyl esters, maleimides, and the like.

FIG. 5 provides further description of such polymeric cross-linkers. The biodegradable region of the crosslinker is represented by ((∧∧∧); ); the activated reactive end-group is represented by ((■); ); and the inert, biocompatible block is represented by ((———); ). Structure A shows a linear water soluble biodegradable polymer end-capped with two reactive functionalities like carbodiimida zole (CDI). The linear water soluble region is a polyalkylene oxide, preferably polyethylene glycol, which is extended with the biodegradable region which is a copolymer or homopolymer of trimethylene carbonate. This polymer is then terminated with CDI. Structure B is a branched or star shaped trifunctional biodegradable polymer which has inert polymer at the center. The inert polymer is extended with oligomeric biodegradable extensions which are then terminated by reactive functional end group. Structures C and D show a multibranched tetrafunctional biodegradable polymer. This polymer again has a water soluble core at the center which is extended by small oligomeric extensions of biodegradable polymer and then terminated with reactive functional groups like carbodiimidazole groups. Structure E shows a multifunctional star or graft type biodegradable polymer. This polymer has a water soluble polymer, like polyalkylene oxide, at the core which is then extended with biodegradable polymer. The biodegradable polymer is terminated with reactive end groups.

The structures shown in FIG. 5 have three common structural features. A water soluble core which is made by a polymer like polyethylene glycol. The core is extended with an oligomeric extension of biodegradable polymer such as polylactic acid. The degree of polymerization of biodegradable core is kept small (preferable less than 10) to maintain water solubility. The molecular weight of PEG is kept less than 35,000 daltons, as higher molecular weights may be difficult to eliminate by the body. The biodegradable polymer is then end-capped with reactive functional groups which are capable of reacting with proteins or its functional groups like amine, thiols and carboxylic acids preferably in water and preferably at pH 4 to 9, more preferably at pH 7.0 to 7.4.

The polymeric crosslinkers may be prepared using variety of different synthetic methods. In a preferred embodiment, the polymer described in structure A can be obtained by a ring opening polymerization of trimethylene carbonate initiated by a dihydroxy compound such as polyethylene glycol molecular weight 2000 d in presence of a suitable catalyst such as stannous octoate. The hydroxy groups of the copolymer thus obtained are then activated with carbodiimidazole (CDI). The CDI activated polymer can then be reacted with a protein concentrate as prepared by this invention to form a crosslinked gel. The reaction conditions of the crosslinking reaction will depend on the nature of activating group employed. Preferred reactions are at pH 5 to 8, most preferred at pH 7.4. The resultant gel degrades due to hydrolysis of the biodegradable polymer such as polytrimethylene carbonate polymer inside the crosslinker. The crosslinking density of the resultant network can be controlled by the overall molecular weight of the structure. A lower molecular weight such as 600 will give much higher crosslinking density as compared to a higher molecular weight crosslinker such a with molecular weight 10000 daltons. The high molecular weight linear crosslinker is preferred in obtaining elastic gels. The reaction between proteins and crosslinkers can be carried out directly on tissues and used as tissue glue. A trifunctional biodegradable crosslinker can be obtained by initiating a polymerization of lactide with trihydroxy polyethylene glycol (ethoxylated trimethylol propane triol) in presence of stannous octoate. The degree of polymerization of lactide is kept less than 5. This is achieved by choosing a molar ratio of PEG with lactide (molar ratio of lactide to PEG is 6, 2 per branch). The PEG-lactate trifunctional polymer is isolated. The hydroxy end groups of copolymers are then activated with CDI. Since this a trifunctional crosslinker, it will give higher crosslinking density as compared to similar molecular weight difunctional crosslinker. This gives additional flexibility in controlling crosslinking density of a crosslinked structure and hence their mechanical and biodegradation properties. The tertafuctional structures are obtained by reacting the polyalkylene oxide copolymer such as TETRONIC® 908 (obtained from BASF corporation) with caprolactorie in presence of stannous octoate. The reaction is carried out in melt at 180° C. for 6 hours under nitrogen atmosphere. The molar ratio of caprolactone to TETRONIC® 908 is kept to 12, which maintains water solubility of TETRONIC® 908-caprolactone copolymer in water. The polymer is activated with CDI and used in crosslinking reaction with proteins.

The protein concentrates prepared by the subject methods also find use in the preparation of novel hydrogel wound dressings. To prepare hydrogel wound dressings from the subject protein concentrates, such as the fibrinogen rich compositions discussed above, where the protein concentrate serves as the "aqueous composition component," the protein concentrates are combined with a macromonomer component and a cross-linking agent under conditions sufficient to produce a hydrogel comprising the protein concentrate composition interspersed throughout the cross-linked gel network.

Macromonomers that find use in the preparation of hydrogel wound dressings are non-toxic, water soluble, non-ionic macromonomers that comprise a polymerizable group, preferably an addition polymerizable group, where macromonomers which can be crosslinked via free radical polymerization are preferred. For example, water soluble polymers having unsaturated polymerizable groups such as acrylate, methacrylate, itaconate, and the like find use. Water soluble polymers of interest which can be modified with unsaturated polymerizable groups include: polyethers, such as polyalkyleneoxide polymers and copolymers, polyethyleneoxide, polyethylene glycol, polyethyleneoxide-polypropyleneoxide block, random or graft copolymers; polyvinyl alcohol; polyvinyl pyrrolidinone; and the like, where polyether polymers or derivatives thereof are particularly preferred as macromonomers. If desired, two or more macromonomers can be copolymerized to obtain suitable hydrogel properties.

While preparation of the hydrogel wound dressings of the subject invention has been described in terms of using the protein concentrates of the present invention as the aqueous composition component that is combined with the macromonomer and the cross-linking agent, other aqueous composition components may also be employed to prepare hydrogel wound dressings according to the subject invention. Other aqueous compositions that may be employed as the aqueous composition component to prepare the subject hydrogel wound dressings include: whole blood, serum, platelet rich plasma (where the platelets may or may not be activated), tissue culture medium, and the like.

The hydrogel wound dressings of the subject invention can be prepared just prior to use or prepared and then stored for subsequent use.

The cross-linking agent is generally a non-toxic polymerization initiator, such as a free radical initiator. Several free radical initiating systems can be used to polymerize the macromonomers containing polymerizable groups such as acrylate or methacrylate. Some of the preferred examples are: DAROCUR® 2959 (initiated around 360 nm), Irgacure 651 (initiated around 360 nm), eosin-triethanol amine (initiated around 510 nm), methylene blue-triethanol amine (initiated around 632 nm), sodium persulfate (initiated around 50° C.), ammonium persulfate (initiated at 50° C.), Glucose oxidase-glucose-ferrous sulfate (initiated around 37° C. in presence of dissolved oxygen in the formulation) and the like.

Optionally, other pharmaceutically acceptable catalysts and cocatylysts can be added to the macromonomer solution to accelerate the polymerization speed and/or to improve its shelf life. For example, small amounts of vinyl pyrrolidinone (concentration around 1-10 micrometers per ml) can be added while using eosin-triethanol photoinitiating system. Inhibitors such as hydroquinone may be added to prevent premature polymerization of macromonomer during its storage. Optionally, the wound dressings described may be prepared with bioactive compounds such as antibiotics to reduce the bacterial infection.

Other agents that may be included in the composition to modulate the ultimate properties of the hydrogel wound dressing prepared therefrom include proteinaceous polymers, such as collagen, other polymeric compounds, such as hyaluronic acid (including derivatives thereof), dextran and the like. Of particular interest are hydrogel wound dressing composites which include, in addition to the hydrogel, at least one of collagen and hyaluronic acid, where in such composites, PEG is the preferred hydrogel.

Hydrogel wound dressings produced in accordance with the present invention can be prepared with desired physical and chemical properties by choosing specific structural features, such as nature of polymerizable group of the macromonomer, the number of polymerizable groups present per macromonomer chain, the chain length and chemical structure of the macromonomer, where the modulation of such parameters to obtain a hydrogel wound dressing of desired characteristics is within the skill of those in the art.

The hydrogel wound dressing composite produced according to the present invention can be produced in various shapes and sizes, such as: films, ropes, rods, plugs, thin or thick sheets, moldings and laminates. Hydrogel wound dressings prepared according to the present invention can be modified further, if necessary or desired, by the addition of pharmaceutically acceptable antioxidants, plasticizers, coloring agents, fillers, fibers, fiber meshes, adhesive backing sheets and the like.

Optionally, the hydrogel wound dressing composite produced according to the present invention can be reinforced with flexible or rigid fibers, fiber mesh, fiber cloth and the like to produce a fiber reinforced hydrogel wound dressing. The insertion of fibers or fibrous structures improves flexibility and tear resistance of the hydrogel wound dressings. Such structures can be produced using any convenient protocol. In a preferred method, the aqueous macromonomer formulation is added to the fiber cloth or net such as cotton gauze. The liquid then flows into the interstices of cloth and is then polymerized to produce a hydrogel, where care is taken to ensure that the fibers or fiber mesh are buried completely inside the hydrogel material. The fibers used in reinforcing the hydrogel network are preferably hydrophilic in nature to ensure better compatibility with the hydrogel network. Also a transparent, flexible plastic film such a polyethylene plastic film which is permeable to oxygen, may be applied on top of the hydrogel wound dressings (opposite side of wound contact) and which may supplied with a plastic mold described in this invention. This plastic film prevents the moisture loss from the hydrogel.

The hydrogel wound dressings produced according to the present invention can be used on variety of wounds. The wounds may be surgical wounds, first, second or third degree burns, skin lesions, decubitus ulcers, venous ulcers, bed sore and the like.

Also provided by the subject invention are kits for preparing the subject fibrinogen rich compositions, kits for preparing the wound dressings and kits for preparing fibrin sealants from the subject fibrinogen rich compositions. Kits for preparing the fibrinogen rich compositions will comprise at least a hydrogel composition and instructions for preparing the fibrinogen rich composition according to the methods of the subject invention, where the instructions may be present in the kit as an insert, incorporated into the containers and/or packaging of the kit, and the like. Kits for preparing the fibrinogen rich compositions may further comprise anticoagulants, e.g. heparin, and one or more containers, e.g. syringes, vials and the like, for use in preparing the fibrinogen rich composition, and the like; where the kit components will generally be sterile, particularly where the ultimate use of the composition involves introduction into a host, e.g. a patient undergoing surgery.

Kits for preparing a fibrin sealant according to the subject invention will comprise at least a fibrinogen rich composition prepared according to the subject invention and a thrombin/calcium setting component present in separate containers. The kit may further comprise a device for delivery the fibrin sealant to a tissue repair site, as described above. Optionally, the kits may also comprise a visualization agent and/or an active agent, preferably present in a biodegradable vehicle. As with the kits for preparing the subject fibrinogen rich compositions, kits for preparing fibrin sealants will also typically comprise instructions for preparing the fibrin sealant, which instructions may be present as a package insert and/or associated with the containers present in the kit and/or packaging of the kit.

Kits for preparing the subject wound dressings will comprise at least the macromonomer component described above and instructions for carrying out the subject methods of preparing the wound dressings. Generally, the kits will also comprise a crosslinking agent. The kits may further comprise a fluid of interest which is to be entrapped in the hydrogel, such as the concentrated protein composition or other fluids, as described above. Other components that may present in the kits include: a container/mold for preparing the wound dressings, and the like.

Also provided are devices for automatically performing one or more of the steps of the subject method to prepare a protein concentrate from an initial protein comprising aqueous composition. The devices of subject invention will generally comprise a container means having a quantity of hydrogel and of sufficient volume for the hydrogel to come into contact with the initial protein composition. The container will further comprise at least one opening for introducing the initial composition into the container and removing the resultant protein concentrate from the container. Generally, the devices will comprise a contacting means for ensuring fluid transfer between the fluid introduced into the container and the hydrogel present therein. In some embodiments, the contacting means is a simple as a polymeric interface layer that is resistant to protein absorption/adsorption. In other embodiments, the contacting means may comprise a filtering means, such as a glass filter or membrane, which is impermeable to the hydrogel. Representative devices according to the subject invention are further described in terms of the figures.

Figure 6:
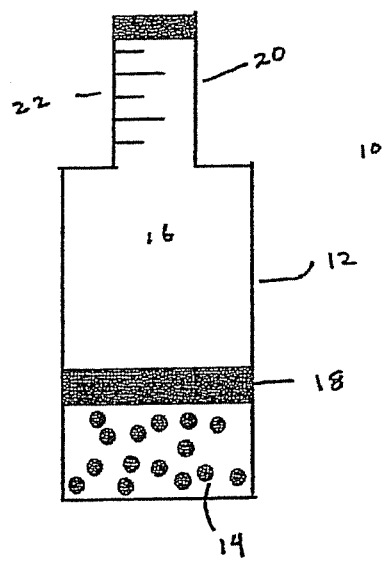
FIG. 6 depicts a first embodiment of a device for producing protein concentrates from a physiological fluid according to the subject invention.
Figure 7A:
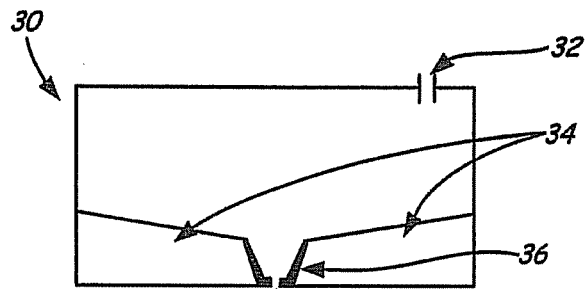
FIG. 7A depicts a second embodiment of a device for producing protein concentrates from a physiological fluid according to the subject invention, and is a cross-sectional view of a vessel with a hydrogel (34), a port for introduction of fluids (32) and an exit port (38) for sterile removal of fluids.
Figure 7B:
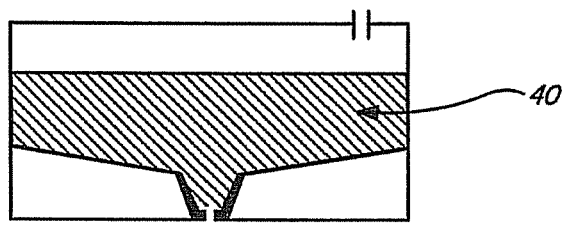
FIG. 7B depicts the embodiment of FIG. 7A, containing fluid (40).
Figure 7C:
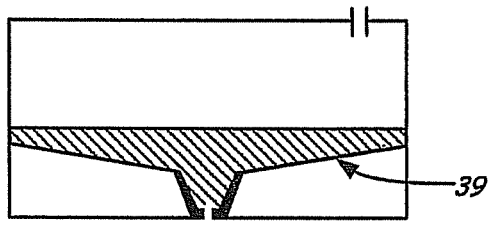
FIG. 7C depicts an alternative embodiment, with the embodiment of FIG. 7A further comprising a membrane (39) over the hydrogel (34).
Figure 7D:
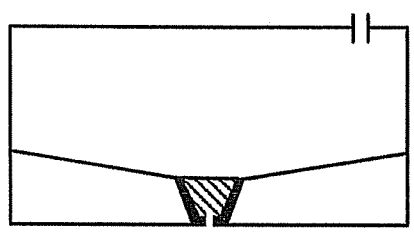
FIG. 7D depicts the embodiment of any of FIGS. 7A-7C with the fluid absorbed into the hydrogel.
Figure 7E:
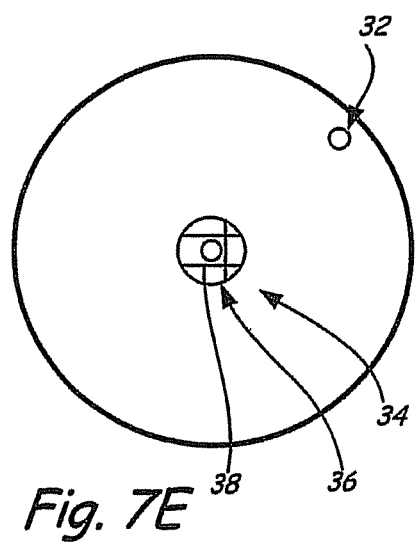
FIG. 7E depicts a top view of the embodiment of FIG. 7A or FIG. 7C.

In FIG. 6 is represented a first device embodiment according to the subject invention. Device 10 is a plastic/glass bottle 12 (could also be a bag) containing hydrogel beads 14 separated from the remainder of the bottle interior by filter mesh 18 which is permeable to liquids but not to the hydrogel beads (i.e. the contacting means). The bottle has a narrow neck 20 that has a volume measurement printed thereon 22. In using this device embodiment, plasma is added to the hydrogel beads and the swelling process is started. The bottle is inverted every 10 minutes to separate the concentrated (the filter prevents the hydrogel from entering the narrow neck region. In the narrow neck region (upon inversion), the volume of plasma is measured. When the desired volume is reached, the concentrated plasma is removed using a suitable technique.

FIG. 7 depicts a second embodiment of a device according to the subject invention. Cylindrical device 30 has entry port 32 for the introduction of fluids into the device. The entry port has a seal (e.g. silicon such as those employed on blood banking blood bags) through which fluids can be sterily introduced into the device or a removable lid (not shown) which can be used in an aseptic technique. Areas 34 contain hydrogel which can absorb fluid and smaller molecules. For use in preparing cryoprecipitate, the hydrogel might have a molecular weight cutoff of about 80,000 so albumin would be absorbed into the hydrogel. In the embodiment shown, the hydrogel compartment would not change physical volume, but has room for the hydrogel to swell and expand. However, other embodiments in which the physical volume of the hydrogel compartment is expandable are envisioned. Collection compartment 36 is a clyindrical shaped cup (though other shaped compartments are also contemplated, such as rectangular etc.) that has walls made of material that does not absorb protein and is also impermeable to fluid. Exit port 38 allows for the sterile removal of fluid, i.e. a septum that can be punctured with a needle. 39 is the top layer of the hydrogel compartment which is a material resistant to protein adsorption/absorption (i.e. the contacting means). The top layer could be fabricated from an appropriate polymeric material, e.g. PEG, or be a membrane which allows for passage of water and other small molecules, such as those used in the purification industry. Use of a membrane provides greater flexibility in the nature of the hydrogel that may be employed, as direct contact of the protein components of the fluid and the hydrogel can be prevented by the membrane. Accordingly, the hydrogel in such devices need not necessarily be a hydrogel that is non-denaturing, as that term is employed above. FIG. 7(*e*) provides a top view of the device. FIGS. 7(*b*) to 7(*d*) show the device in use. In using the device to prepare a protein concentrate from an aqueous composition, fluid 40 is introduced through port 32. Water and other small molecules are absorbed into hydrogel 34. As the fluid is absorbed, the level of the fluid falls until it reaches the top of the collection compartment 36. Concentrate is then removed from the collection compartment through exit 38. The device is configured with dimensions chosen based on the intended nature of use. For example, in the preparation of a fibrinogen rich composition from plasma, in many situations the device will have dimensions sufficient to hold up to 1 unit of blood. Where desired, the entire device can be rotated at low rpm (usually less than 500) to facilitate mixing of the fluid and reduction of fouling by proteins of the top or interface layer of the hydrogel or the membrane 39 covering the hydrogel component. Furthermore, coatings or active coatings or gel microspheres with active coatings could be placed on the periphery of the device (on the inside of the outside wall of the device above the hydrogel compartment) which would specifically absorb albumin, other proteins or specific cell types for cell purification. If the membrane 39 over the fluid absorbing component 34 is properly selected, a wider range of swelling polymers may be employed as the hydrogel component as mentioned above. Accordingly, polymer compositions such as those found in disposable diapers to absorb urine may be employed. Alternatively, the device could operate with hydrogel beads that are excluded from the collection cup 36 by having a means over the collection cup.

The following examples are offered by way of illustration and not by way of limitation.

EXPERIMENTAL

A. Materials and Methods

Polyethylene glycols (Merck, mol. wt 20000 and BDH mol. wt 6000) were used as received. PLURONIC® and TETRONIC® polyols were purchased from BASF corporation. Photoinitiator DAROCUR® 2959 was purchased from Ciba Geigy. The biodegradable polymers like polylactic acid, polyglycolic acid are purchased from Polysciences. All other reagents, solvents are of reagent grade and are purchased from commercial sources such as Fluka, Aldrich and Sigma. Small laboratory equipment was purchased from Fisher or Cole-Parmer.

B. Synthesis of Hydrogels

1. Synthesis of Polyethylene Glycol Diacrylate

In a 1,000 ml 3 neck reaction flask, attached with condenser, nitrogen inlet and thermometer, 100 grams of PEG (molecular weight 20,000 daltons) and 600 ml dry toluene are added. After distilling 100 ml of toluene from the flask, the PEG solution is cooled to 50-60° C. To this mixture, 2.1 ml of triethylamine and 1.2 ml of acryloyl chloride is added under nitrogen atmosphere. The reaction is stirred for 10-12 hours at ambient temperature under nitrogen atmosphere. The triethylamine hydrochloride (a reaction byproduct) is removed by filtration and the product is recovered by pouring the filtrate in to large excess hexane. It is further purified by several dissolution precipitation steps using tetrahydrofuran (THF)-hexane as solvent-nonsolvent respectively. The product is further dried at 40° C. under vacuum until constant weight is observed. Yield 60 gram.

Other macromonomer containing PEG with different molecular weights, and different number of unsaturated groups are easily synthesized using the procedure given above. For example, 30 grams PEG molecular weight 6000 daltons is reacted with 2.67 g acryloyl chloride and 3.03 g triethyl amine using a similar procedure mentioned above to give PEG 6,000 diacrylate. Similarly PEG 10000 diacrylate is prepared by reacting 30 grams of PEG molecular weight 10,000 Da with 1.82 g of triethyl amine and 1.61 g of acryloyl chloride. Polyethyleneoxide (PEO) molecular weight 35,000 Da (30 g) is reacted with 0.52 g of triethyl amine and 0.46 g of acryloyl chloride to get a corresponding diacrylate derivative. Some polyethylene glycol based macromonomers may also be purchased using commercial sources such as Sartomer, Polysciences.

2. Synthesis of Polyethyleneoxide-Polypropyleneoxide-Polyethyleneoxide Diacrylate 50 grams of PLURONIC® F127 (a PEO-PPO-PEO block copolymer with 70% PEO content, molecular weight 12500 daltons, purchased from BASF corporation) is dried under vacuum at 80-100° C. The polymeric diol is then transferred to a 3 neck reaction flask equipped with nitrogen inlet and thermometer. 500 ml toluene, 3.3 ml of triethylamine amine and 1.9 ml of acryloyl chloride are added to the reaction mixture under dry nitrogen atmosphere. The reaction mixture is stirred overnight and filtered to remove triethylamine hydrochloride. The filtrate is added to 3000 ml hexane to precipitate the diacrylate derivative of PLURONIC® F127. The macromonomer is purified by several dissolution-precipitation steps from THF-hexane solvent-nonsolvent system. Finally the diacrylate is dried under vacuum at 40° C. to a constant weight.

Other derivatives of PLURONICS® with different arrangement of PEO-PPO blocks and with different HLB values can also be acrylated in a similar manner.

3. Preparation of Sterile Gels Using Photopolymerization Method 10 grams of PEG diacrylate, synthesized by a procedure described above, are dissolved in 20 grams of phosphate buffer solution (pH 7.4, 0.2 g/L KCl, 0.2 g/L of $KH_2PO_4$, 8.0 g/L of NaCl and 1.15 g/L $Na_2HPO_4$). To this solution 600 µl of photoinitiator solution (300 mg of DAROCUR® 2959, Ciba Geigy, dissolved in 700 mg ethanol) is added. The following procedure is carried out in a sterile hood. The aqueous macromonomer solution is sterile filtered using 50 ml syringe and 0.2 mm syringe filter. 200 µl of sterile solution is transferred into transparent plastic mold (a single well of a sterile 96 well tissue culture plate). The solution is then exposed to long wavelength UV light (Blak Ray light source, model 3-100A, Flood 365 nm, intensity 10 mW/cm$^2$) for 120 seconds. The polymerized gel is removed from the mold. The resultant gel may be freeze dried or freeze dried coupled with limited hydration following preparation. Several of such hydrogel beads are synthesized and stored in a sterile container for further use.

4. Preparation of Sterile Gel Microspheres 5 grams of PEG diacrylate, molecular weight 10,000 daltons are dissolved in 15 grams of triethanolamine/triethanolamine hydrochloride solution (90 mM, pH=7.4) in a 50 ml amber colored glass bottle. To this solution 30 µl of Eosin Y solution (1 mg/ml in PBS) and 30 µl vinyl pyrrolidinone are added. The mixture is protected from visible light using aluminum foil. The following operations are carried out in a sterile hood: The macromonomer solution is filtered using 50 ml syringe and 0.2 µm syringe filter. The filtered sterile solution is filled into 50 ml plastic syringe (wrapped in aluminum foil for protection against light) with 22 gauge needle. A 100 ml of sterile mineral oil which is constantly being stirred using a magnetic stir bar is exposed to green light source (American Argon ion laser, Model 905 emitting at 532 nm, 100 mW/cm$^2$). The macromonomer solution is flushed out of needle and the droplets are collected into sterile mineral oil which is under green light irradiation. After 5 minutes of irradiation of monomer solution to green light, the photopolymerized hydrogel beads are separated from mineral oil by filtration. The hydrogel beads are further washed with sterile hexane to remove traces of mineral oil. The hydrogels beads are then stored in sterile saline solution for 5 hours to remove initiator fragments, unreacted or uncrosslinked macromonomer etc. The washed beads are then isolated by filtration and lyophilized under sterile conditions.

5. Synthesis of Multifunctional Thermosensitive Macromonomer 30 g of TETRONIC® 908 polyol is dissolved in 400 ml dry benzene. 100 ml of benzene is distilled to remove traces of water from the polyol. The solution is cooled to 30° C. and 1.45 g triethylamine and 1.90 g acryloyl chloride are added. The reaction mixture is refluxed for 1 h under argon atmosphere. It is then cooled and then filtered to removed triethylamine hydrochloride. The filtrate is then added to 2000 ml hexane to precipitate the polymer. The polymer is purified by several precipitations from THF-hexane solvent-nonsolvent system. Further solvent removal/drying is achieved by vacuum drying overnight at 60° C.

Figure 3:
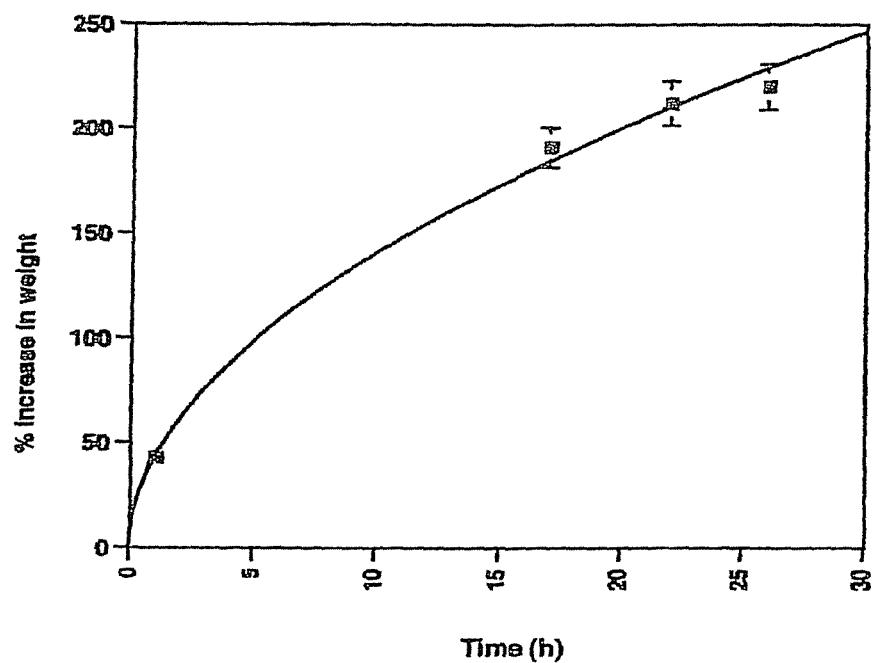
FIG. 3 provides a graphical representation of the water absorptive properties of a PEG 20,000 diacrylate hydrogel.

6. Preparation of Hydrogels by Radical Thermal Polymerization Method 10 grams of PEG diacrylate molecular weight 20,000 daltons are dissolved in 20 gram of PBS buffer (pH=7.4). To this solution 300 mg ammonium persulfate are added as a thermal free radical polymerization catalyst and the mixture is sterile filtered. This sterile solution is then transferred into several sterile 5-10 mm diameter glass test tubes. The test tubes are then capped and transferred into lab oven maintained at 70° C. After 15 minutes, the test tubes are removed, cooled and the polymerized gels are removed by breaking the glass container. The gel rods are cut into small 1-2 cm pieces and stored. Sterility of gel rods is maintained throughout the entire operation. The resultant hydrogels, when contacted with water, absorb water over time and increase in mass, as shown in FIG. 3.

C. Synthesis of Drug Compositions

1. Preparation of Rifampin Sulfate Loaded Polylactic Acid Particles

In a 50 ml glass beaker, 2 g of polylactic acid is dissolved in 20 ml methylene chloride. To this mixture is added 1 g of gentamycin sulfate. The resultant slurry is thoroughly mixed and poured on a glass plate. After initial methylene chloride removal from the slurry, the partially dried film is dried in vacuum oven at 40° C. for 48 hours. The resultant gentamycin-PLA composite is pulverized into small particles by cryogenic grinding at liquid nitrogen temperature. The particles may be sieved to obtain a particular size distribution.

2. Preparation of Gentamycin Loaded Microspheres of Polylactate-co-polyglycolate (50:50) Polymer 0.1 g of Rifampin is dissolved in 5 ml PBS (pH 7.2) containing 10 mg of bovine serum albumin. The resultant aqueous solution is added to 30 ml methylene chloride containing 5 grams of polymer and then emulsified by a brief sonification for 30 seconds. The water-in-oil (W/O) emulsion is reemulsified in 2,000 ml 0.1% (w/v) polyvinyl alcohol (PVA) with stirring for 3 hours at room temperature. The hardened microspheres are washed three times with PBS buffer to remove unencapsulated Rifampin. The microspheres are recovered by centrifugation and freeze-drying. The residual solvent is removed by drying the microspheres in vacuum oven at 37° C. for 48 hours. Alternatively 0.1 g of Rifampin is dissolved in 5 ml acetone. The acetone solution is then added to 30 ml solution of polylactate-co-polylactate (50:50) in methylene chloride (4% wt/v). The mixture is then spray dried using standard laboratory spray dried.

D. Preparation of Fibrinogen Composition Using Hydrogels

1. In a sterile glass bottle, having a rubber septum cap and containing heparin anticoagulant, 20 ml of patient's blood is transferred using a sterile needle transfer technique or standard Schlenk line techniques. The tube is then centrifuged at 3,200 rpm for 10 minutes. The resultant blood plasma is transferred using a sterile needle transfer technique to another sterile bottle containing 4 g of sterile PEG 20,000 diacrylate gel rods prepared by the method described in example 6 above. The hydrogel selectively absorbs water and other low molecular weight proteins such as albumin, plasminogen and compounds like heparin leaving behind a concentrated solution of fibrinogen and Factor XIII. The hydrogel absorption time (usually minutes to several hours) is controlled so as to obtain a desired volume/concentration of a final solution (typically 90-95% water is removed from the plasma). This concentrated protein solution gels with commercially available thrombin, Ca$^{+2}$ ion solution.

2. Preparation with Hydrogel Beads

Figure 1B:
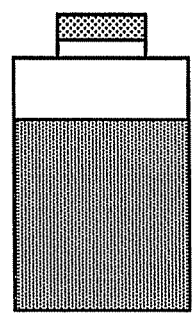
FIG. 1B provides a schematic representation of another inventive method of preparing fibrinogen rich compositions.
Figure 1C:
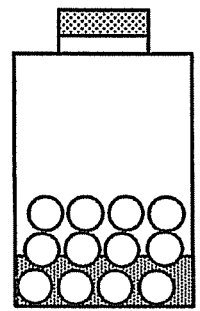
FIG. 1C provides a schematic representation of another inventive method of preparing fibrinogen rich compositions.
Figure 2A:
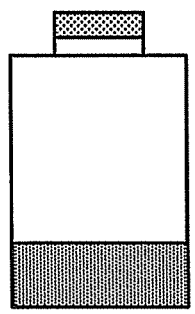
FIGS. 2A-2B provide a schematic representation of the preparation of a drug loaded fibrin gels according to the subject invention. In these figures, vial A (FIG. 2A) contains controlled release microspheres encapsulated with bioactive compounds and calcium salt. Vial B (FIG. 2B) contains all the components of a fibrin glue system (i.e. fibrinogen, thrombin etc.) except calcium, in a lyophilized form. Vial A and B are reconstituted with sterile saline solution and used as a fibrin glue system. A and B are mixed and applied in situ in a surgical field using a suitable surgical device.
Figure 2B:
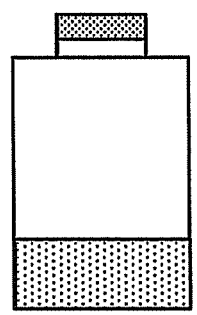
Figure 4:
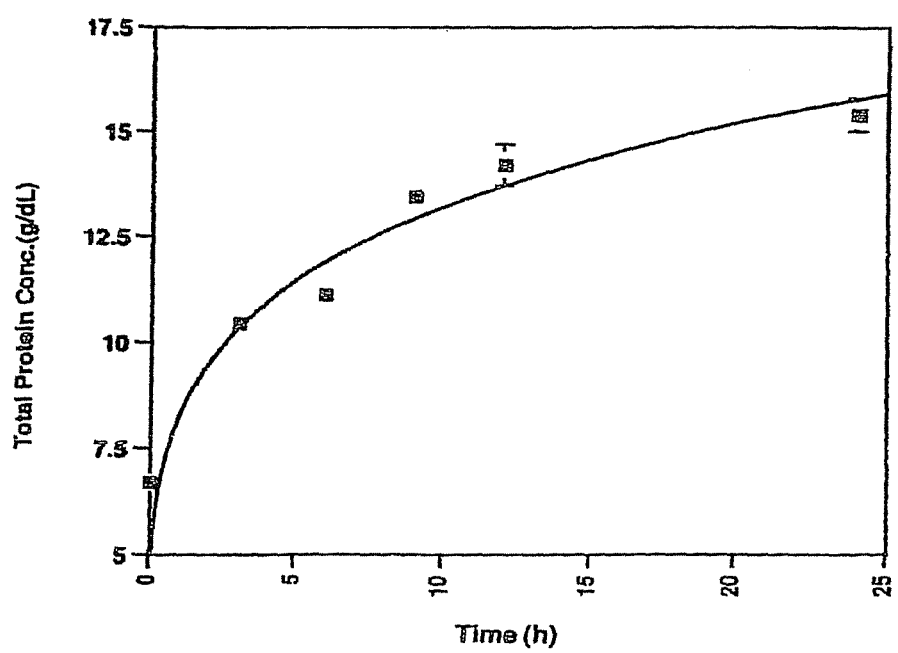
FIG. 4 provides a graphical representation of the protein concentration over time in a protein comprising aqueous composition contacted with a hydrogel according to the subject invention.
Figure 5A:
FIGS. 5A-5E provide a schematic representation of various polymeric crosslinking agents of the subject invention. In these figures ((/\/\/\)) represents a biodegradable component such as polyhydroxy acids, polylactones and their copolymers, or synthetic peptide sequences which are cleaved by enzymes inside the human body; ((▬)) represents a reactive functional group such as carbodiimiddazole, aldehyde, epoxide, n-hydroxysucciniinide and the like; ( (————)) represents a biocompatible inert component, such as polyethylene glycol, dextran, polyvinyl alcohol; ((|||||)) represents a copolymer of trimethylene carbonate and lactones or a synthetic peptide sequence which is cleavable by human enzymes.
Figure 5B:
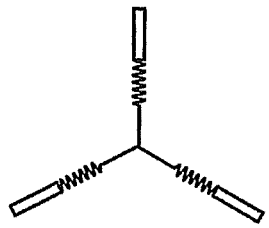
Figure 5C:
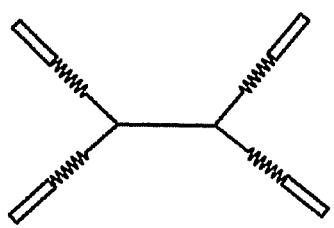
Figure 5D:
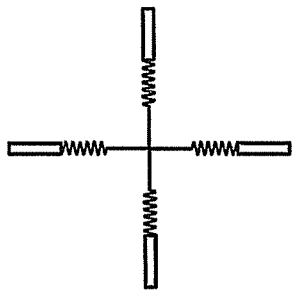
Figure 5E:
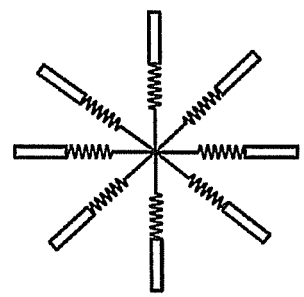

Blood plasma is concentrated with hydrogel beads using a method analogous to that described in example D1, above. The process is shown schematically in FIG. 1. In the schematic shown in FIG. 1, dry or partially dry hydrogel beads are placed in a sterile tube as shown in FIG. 1A. Next, a blood plasma solution is transferred to the tube as shown in FIG. B. The mixture is allowed to remain in contact for a sufficient period of time for the hydrogel beads to selectively absorb water from the plasma, whereby a fibrinogen rich composition is produced, as shown in FIG. 1C. A small amount of plasma is taken out periodically and is analyzed for total protein concentration using a biurette method, the results of which are shown in FIG. 4.

E. Preparation of Colored Fibrin Adhesive Solution

1. Indocyanine Green 5 ml of concentrated solution of fibrinogen solution as prepared above in Example D is added to a sterile bottle containing 0.1 ml indocyanine green solution in PBS (conc.

0.1 to 10 mg/ml). The green precursor solution is easy to visualize and apply under normal and laparoscopic surgical environment. This green solution is used with thrombin solution as a colored fibrin adhesive system.

2. Preparation of Fluorescent Adhesive Formulation 5 ml of concentrated solution of fibrinogen solution is added to a sterile bottle containing 0.1 ml sodium fluorescine in solution in PBS (conc. 0.1 to 10 mg/ml). The light green fluorescent precursor solution is easy to visualize and apply under normal and laparoscopic surgical environment. This green solution is used with thrombin solution as a colored fibrin adhesive system.

F. Preparation of Fibrin-Biodegradable Microparticle Composite 5 ml concentrated solution of fibrinogen or the commercial fibrinogen containing precursor of fibrin adhesive is mixed with 0.5 grams polylactic acid or polyhydroxy acid microspheres loaded with bioactive compound such as gentamycin. The resultant slurry is transported to a localized disease site inside the human or animal body using minimally invasive surgical device such as laparoscope and crosslinked in situ using thrombin solution.

G. Preparation of Protein Composites Crosslinked with Biodegradable Polymeric Crosslinking Agents 1. Synthesis of Water Soluble Difuctional, Biodegradable Crosslinker Based on Polyalkylene Oxide Synthesis of polyethylene glycol-trimethylene carbonate polyol-30 g of polyethylene glycol having a molecular weight 2000 is dried at 90-100° C. in a glass sealing tube. The tube is then cooled and transferred inside an air bag where 12.24 g of trimethylene carbonate and 50 mg of stannous octoate are added to the tube. The glass tube is then sealed under nitrogen atmosphere and heated with stirring at 155° C. and maintained at this temperature for 6 hours. The polyethylene glycol-polytrimethylene carbonate polymer is cooled and recovered by breaking the glass sealing tube. It is further purified by several precipitations from toluene-hexane solvent-nonsolvent system. The product is dried in vacuum at 40° C. and used immediately in the activation reaction.

2. Synthesis of Water Soluble, Tetrafunctionai Crosslinker Based on Polyaikylene Oxide Synthesis of TETRONIC® 908-caprolactone polyol (PCLP)-30 g of TETRONIC® 908 is charged in a dry 3 neck flask equipped with magnetic stirrer and vacuum inlet. The flask is then heated in a silicone oil bath at 100° C. for 12 hours to dry the TETRONIC® 908. The flask is cooled to room temperature and 1.642 g of caprolactone and 0.02 g of stannous 2-ethylhexanoate are added to the flask. The flask is heated to 180° C. for 6 hours under nitrogen atmosphere. The reaction is product is then dissolved in 200 ml dry toluene (warming of toluene accelerates dissolution). The toluene solution is added to 2,000 ml dry heptane with constant stirring. The product is isolated by filtration. Further purification is accomplished by precipitation of toluene solution of PCLP in heptane. The product is dried in vacuum at 40° C. and used immediately in the activation reaction.

3. a) Activation Polyalkyleneoxide Lactate Copolymer with Carbodiimidazole:

30 g of TETRONIC® 908-caprolactone copolymer is dissolved in 400 ml dry benzene. About 100 ml of benzene is distilled off and the solution is cooled to 50° C. 2.50 g of succinic anhydride is added to reaction mixture. The mixture is refluxed for 5 hours under nitrogen atmosphere. At the end of 5 hour period, the solution cooled and then added to 4,000 ml hexane to precipitate the polymer. It is further purified by repeated (3 times) precipitation from toluene-hexane system. The polymer is dried under vacuum at 40° C.

b) Activation Polyalkyleneoxide Lactate Copolymer with N-hydroxysuccinimidyl Ester:

30 g of Tetronic 908-caprolactone copolymer is dissolved in 400 ml dry benzene. About 100 ml of benzene is distilled off and the solution is cooled to 50° C. 2.50 g of succinic anhydride is added to reaction mixture. The mixture is refluxed for 5 hours under nitrogen atmosphere. At the end of 5 hour period, the solution cooled and then added to 4,000 ml hexane to precipitate the polymer. It is further purified by repeated (3 times) precipitation from toluene-hexane system. The polymer is dried under vacuum at 40° C.

c) Activation of Acid Terminated Polymer with Dicyclohexylcarbodiimide (DCC)

10 g of TETRONIC® 908-caprolactone succinate prepared by method described above is dissolved in 100 ml dry methylene chloride. The mixture is cooled to 0° C. in ice bath and 0.5 g of 4-dimthylaminopyridine and 1 g of dicyclohexylcarbodiimide (DCC) are added. The mixture is stirred at 0° C. for 6 hour and filtered. The filtrate is then added to 2,000 ml dry hexane to precipitate the activated succinimydyl ester. The product is isolated by filtration, dried under vacuum and stored under argon at 4° C.

4. Preparation of Crosslinked Protein Composites

The CDI/succinimydil activated crosslinker polymers as prepared above are dissolved in aqueous buffer solution and reacted with albumin rich solutions to form a gel.

H. Preparation of Hydrogel Wound Dressings

1. Preparation of Sterile Hydrogel Wound Dressings using Photopolymerization Method 5 grams of PEG 10,000 diacrylate, synthesized by a procedure described in example B1, is dissolved in 20 grams of phosphate buffer solution (pH 7.4, 0.2 g/L KCl, 0.2 g/L of $KH_2PO_4$, 8.0 g/L of NaCl and 1.15 g/L $Na_2HPO_4$). To this solution 100 microliter of a photoinitiator solution (300 mg of DAROCUR® 2959, Ciba Geigy, dissolved in 700 mg ethanol) is added. The following procedure is carried out in a sterile hood: The aqueous macromonomer solution containing photoinitiator is sterile filtered using 50 ml syringe and 0.2 mm syringe filter. About 10-12 mL of sterile solution is transferred into transparent plastic mold (10 cm×5 cm×2 mm). The solution is then exposed to long wavelength UV light (Blak Ray light source, model 3-100A, Flood 365 nm, intensity 30 mW/cm$^2$) for 5 minutes. The polymerized, flexible gel is removed from the mold. This sterile gel can be directly applied over the wound.

2. Gamma Radiation Crosslinking of Macromonomers 3 g of PEG 20,000 diacrylate is dissolved in 12 ml PBS buffer. The aqueous monomer solutions is sterile filtered into glass mold (cavity size 10 cm×5 cm×2 mm). The solution is then irradiated at ambient temperature with a $^{60}$Co source with doses up to 200 kGy at a dose rate of 1 kGy/h. After irradiation, the sterile crosslinked gel is removed from the mold and used as wound dressing.

3. Preparation of Sterile Lyophilized Macromonomer Formulation 3 grams of PEG 10,000 diacrylate, synthesized by a procedure described in example, is dissolved in 12 grams of phosphate buffer solution (pH 7.4, 0.2 g/L KCl, 0.2 g/L of $KH_2PO_4$, 8.0 g/L of NaCl and 1.15 g/L $Na_2HPO_4$). To this solution 60 microliter of photoinitiator solution (300 mg of DAROCUR® 2959, Ciba Geigy, dissolved in 700 mg ethanol) is added. The aqueous macromonomer solution containing photoinitiator is sterile filtered using 50 ml syringe and 0.2 mm syringe into a sterile amber colored 25 ml glass bottle. The solution is lyophilized while maintaining sterility to remove water. At the end of the lyophilization cycle, the vial is capped with a sterile rubber septum. The lyophilized macromonomer powder containing photoinitiator is used in making 'in situ' formable wound dressings.

4. Autologus or Single Donor Single Donor Blood or Blood Components Encapsulated Wound Dressing 15-20 ml of fresh human or animal blood is withdrawn in a standard syringe or similar medical device containing anticoagulant such as heparin or acid citrate buffer (2% glucose, 0.15M citrate, pH 4.2, 1 ml buffer per 10 ml blood). The blood is then centrifuged in order to separate out the blood plasma. The plasma is then removed from the centrifuge tube and transferred into a sterile macromonomer lyophilized powder containing initiator (such as made in example 3 to make a 5-40% solution, preferably 10% solution of the macromonomer in plasma (some proteins such as fibrinogen may precipitate depending on the macromonomer and its concentration used). The macromonomer-plasma solution/dispersion is then transferred into sterile plastic dish or mold of size 10 cm×5 cm×2 mm using a sterile syringe and needle. The contents of the mold are then exposed to long UV irradiation for 3 minutes to crosslink the macromonomer. The crosslinked sterile hydrogel can be directly applied on the wound.

In another variation of this procedure, 15-20 ml of fresh human or animal blood is withdrawn in a closed sterile plastic or glass vial without anticoagulant. The blood is allowed to coagulate for 30 to 60 minutes. The top clear solution (serum) is withdrawn from the vial using a syringe. This serum is then used in preparation of hydrogel dressing using a procedure mentioned previously.

5. Preparation of Hydrogel Wound Dressing Containing Platelets 15 to 20 ml of fresh human or animal blood is isolated using a standard procedure. The blood is then centrifuged at low rpm (around 3,000 rpm) in order to separate the platelet rich plasma. The platelet rich plasma is then added to a sterile lyophilized macromonomer initiator formulation such as described in example 3. The entire mixture is then poured into sterile plastic or glass mold of suitable size for example 10 cm×5 cm×2 mm cavity size and exposed to long UV or visible light for 3 minutes to crosslink macromonomer. The gel containing encapsulated platelets is removed and may be directly applied on the wound.

Platelets may be activated using thrombin or suitable activating agent before or after the encapsulation process. The activated platelets release platelets derived growth factors which are then released in controlled manner by the hydrogel matrix.

6. Preparation of Hydrogel Wound Dressing Containing Tissue Culture Medium (without Serum)

A sterile amber colored glass vial containing 3 grams macromonomer and photoinitiator (similar to described in example 6) is dissolved in 12 ml tissue culture medium (for example Dulbecco's modification of Eagle's medium, a medium suitable for culturing human foreskin fibroblasts). The macromonomer solution in tissue culture medium is then sterile filtered into a plastic mold of desired shape for example 10 cm×5 cm×2 mm size and exposed to long UV light as mentioned in previous examples. The polymerized hydrogel is then removed from the mold and used as wound dressing.

7. Preparation of Hydrogel Wound Dressing Containing Tissue Culture Medium (with Autologus or Single Donor Blood Serum)

15-20 ml of fresh human or animal blood is withdrawn in a standard syringe and allowed to stand to coagulate for 0.25 to 2 hours. The blood is then centrifuged in order to separate out the blood serum. 2 ml of this blood serum is then mixed with 18 ml of tissue culture medium such as described in previous example. 12 ml of this mixture is then added to a lyophilized macromonomer formulation prepared as described in example 6. This macromonomer is then sterile filtered into a plastic sterile mold 10 cm×5 cm×2 mm size and exposed to long UV light for 3 minutes. The crosslinked macromonomer or hydrogel contains tissue culture medium and serum.

8. Preparation of Polyalkylene Oxide-hyaluronic Acid Hydrogel Wound Dressing 3 grams of PEG diacrylate, synthesized by a procedure described in example B1, is dissolved in 12 grams of phosphate buffer solution (pH 7.2, 0.2 g/L KCl, 0.2 g/L of $KH_2PO_4$, 8.0 g/L of NaCl and 1.15 g/L $Na_2HPO_4$ and 0.5% sodium hyaluronate). To this solution 60 microliter of photoinitiator solution (300 mg of DAROCUR® 2959, Ciba Geigy, dissolved in 700 mg ethanol) is added. The following procedure is carried out in a sterile hood.

The aqueous macromonomer solution containing photoinitiator and hyaluronic acid is sterile filtered using 50 ml syringe and 0.2 μm syringe filter. About 10-12 mL of sterile solution is transferred into transparent plastic mold (cavity size 10 cm×5 cm×2 mm). The solution is then exposed to long wavelength UV light (Blak Ray light source, model 3-100A, Flood 365 rim, intensity 30 $mW/cm^2$) for 5 minutes. The polymerized, flexible gel is removed from the mold. This sterile gel can be directly applied over the wound.

9. Preparation of Polyalkylene Oxide-collagen Composite Hydrogel Wound Dressing 3 grains of PEG diacrylate, synthesized by a procedure described in example B1, is dissolved in 12 grams of phosphate buffer solution (pH 7.4, 0.2 g/L KCl, 0.2 g/L of $KH_2PO_4$, 8.0 g/L of NaCl and 1.15 g/L $Na_2HPO_4$). 60 microliter of photoinitiator solution (300 mg of DAROCUR® 2959, Ciba Geigy, dissolved in 700 mg ethanol) is added to the macromonomer solution and the mixture is then sterile filtered into 25 ml sterile glass vial. 100 mg of sterile collagen lyophilized powder is then added to the macromonomer solution. The dispersion is well mixed and then transferred into transparent plastic mold (cavity size 10 cm×5 cm×2 mm). The dispersion is then exposed to long wavelength UV light (Blak Ray light source, model 3-100A, Flood 365 nm, intensity 30 $mW/cm^2$) for 5 minutes. The polymerized, flexible gel is then removed from the mold and used as polyalkyleneoxide-collagen hydrogel wound dressing.

10. In situ Formation of Tissue Conformal Wound Dressing Using Aqueous Thermosensitive Macromonomer Solutions 10 grams of thermosensitive macromonomer (synthesized as described in example B5) is dissolved in 20 ml cold (0-15° C.) PBS solution. To this solution, 90 microliter of DAROCUR® 2959 solution (300 mg in 0.7 ml ethanol) is added and mixed. The cold solution is then transferred into 50 ml cold syringe and filtered using 0.2 micron syringe filter into another vial (the solution should be cold (0-5° C.) in order to filter). The filtered cold solution is directly applied over wound surface or injected into a wound cavity. The cold solution conforms to the wound geometry or cavity and the body temperature causes physical gelation of the macromonomer. The physically gelled solution is then irradiated with long UV light to crosslink the macromonomer solution. The light induces chemical crosslinking and forms a chemically crosslinked hydrogel which has good absorptive and mechanical properties. The polymerized gel is also non-adherent to the tissue and can be easily removed from the wound site.

It is evident from the above results and discussion that an improved method of preparing protein concentrates, and particularly fibrinogen rich compositions, from blood compositions such as whole blood and plasma are provided. The subject methods are simple and easy to practice and require less time than prior methods of preparing fibrinogen rich compositions. Furthermore, the above methods allow greater control over the composition of the fibrinogen rich compositions than do prior preparation methods. Importantly, the subject methods provide for protein concentrates in which the proteins are not denatured.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of preparing a fibrinogen rich composition said method comprising:
   providing a mammalian blood plasma or preparing mammalian blood plasma from whole blood by removal of red blood cells and white blood cells without centrifugation,
   contacting the plasma with a biocompatible hydrogel comprising a polyether,
   maintaining the contact with the plasma to produce a swollen hydrogel and a fibrinogen rich phase, and
   passively separating said fibrinogen rich phase from said swollen hydrogel without centrifugation.

2. The method according to claim 1, wherein said plasma comprises an anticoagulant.

3. The method of claim 1 wherein the plasma and the hydrogel are combined in a bag.

4. The method of claim 1 wherein the wherein the plasma and the hydrogel are combined in a container, and further comprising inverting the container.

5. The method of claim 4 wherein the container holds no more than one unit of blood.

6. The method of claim 1 wherein the hydrogel has a molecular weight cut-off of 80,000 Daltons.

7. The method of claim 1 wherein the hydrogel comprises a plurality of rods made of the hydrogel.

8. The method of claim 1 wherein the hydrogel comprises a plurality of beads made of the hydrogel.

9. The method of claim 1 wherein the hydrogel comprises cross-linked polyethylene glycols.

10. The method of claim 1 further comprising mixing the fibrinogen rich composition with thrombin.

11. The method of claim 1 further comprising mixing the fibrinogen rich composition with a water soluble multi-functional synthetic cross-linker for cross-linking proteins in the composition.

12. The method of claim 1 wherein preparing the plasma from whole blood by removal of red blood cells and white blood cells from the blood without centrifugation comprises binding the blood cells with the hydrogel.

13. The method of claim 12 wherein the binding of the blood cells is accomplished with a coating on the hydrogel.

14. The method of claim 13 wherein a plurality of hydrogel beads comprise the coating.

* * * * *